(12) United States Patent
Koike et al.

(10) Patent No.: US 7,804,592 B2
(45) Date of Patent: Sep. 28, 2010

(54) METHOD FOR MEASURING A SURFACE PLASMON RESONANCE AND NOBLE METAL COMPOUND USED FOR THE SAME

(75) Inventors: Tohru Koike, Hiroshima (JP); Akihiko Kawasaki, Amagasaki (JP); Tatsuhiro Kobashi, Amagasaki (JP); Makoto Takahagi, Amagasaki (JP)

(73) Assignee: NARD Institute, Ltd. (JP)

( * ) Notice: Subject to any disclaimer, the term of this patent is extended or adjusted under 35 U.S.C. 154(b) by 1063 days.

(21) Appl. No.: 10/575,714

(22) PCT Filed: Oct. 12, 2004

(86) PCT No.: PCT/JP2004/015347
§ 371 (c)(1),
(2), (4) Date: May 8, 2006

(87) PCT Pub. No.: WO2005/038442
PCT Pub. Date: Apr. 28, 2005

(65) Prior Publication Data
US 2009/0185181 A1    Jul. 23, 2009

(30) Foreign Application Priority Data

| Oct. 16, 2003 | (JP) | 2003-356934 |
| Feb. 20, 2004 | (JP) | 2004-044035 |
| Mar. 29, 2004 | (JP) | 2004-094160 |

(51) Int. Cl.
*G01J 3/44* (2006.01)

(52) U.S. Cl. .............. 356/301; 546/2; 546/12; 546/256

(58) Field of Classification Search .......... 356/300, 356/301, 445; 546/264, 200, 2, 12, 256
See application file for complete search history.

(56) References Cited

U.S. PATENT DOCUMENTS 5,313,264 A    5/1994    Ivarsson et al.

(Continued)

FOREIGN PATENT DOCUMENTS

EP    0587008    2/1999

(Continued)

OTHER PUBLICATIONS

The Official Action issued for the corresponding Russian Patent Appl. No. 2006116577.

(Continued)

*Primary Examiner*—Tarifur Chowdhury
*Assistant Examiner*—Abdullahi Nur
(74) *Attorney, Agent, or Firm*—Gerald E. Hespos; Michael J. Porco

(57) ABSTRACT

The present invention provides a method for measuring a surface plasmon resonance, the method enabling easy detection of the existence of a phosphorylated peptide (protein) and determination whether a peptide is phosphorylated or not in biological materials. The present invention also provides a noble metal compound having high capability of coordination to a phosphorylated peptide, and being conveniently usable in the method. A first method for measuring surface plasmon resonance of the present invention comprises: placing a noble metal compound on a bottom face of a prism, irradiating a light to the prism to detect a reflected light, wherein, the noble metal compound has substituents of following formula (I) on a side opposite to a side contacting the prism, and a subject sample is added to a side having the substituent groups (I) in the noble metal compound.

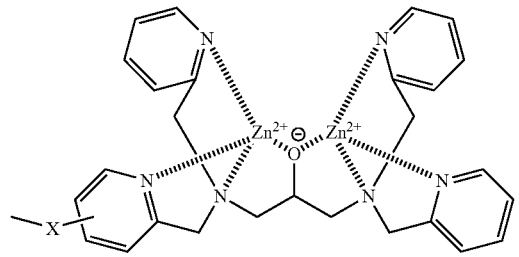

(I)

[wherein, X represents a linker group]

2 Claims, 5 Drawing Sheets

U.S. PATENT DOCUMENTS

| | | | |
|---|---|---|---|
| 5,341,215 A * | 8/1994 | Seher | 356/445 |
| 5,376,556 A | 12/1994 | Tarcha et al. | |
| 5,874,584 A | 2/1999 | Wear et al. | |
| 6,120,768 A | 9/2000 | Griffiths et al. | |
| 6,143,879 A | 11/2000 | Que, Jr. et al. | |
| 6,628,376 B1 | 9/2003 | Nikitin et al. | |
| 7,358,363 B2 * | 4/2008 | Koike et al. | 546/27 |
| 2004/0198712 A1 | 10/2004 | Koike et al. | |
| 2005/0038258 A1 | 2/2005 | Koike et al. | |

FOREIGN PATENT DOCUMENTS

| | | |
|---|---|---|
| EP | 1674857 A1 | 6/2006 |
| JP | 6174723 | 6/1994 |
| JP | 7157487 | 6/1995 |
| JP | 7-174693 | 7/1995 |
| JP | 9-257578 | 10/1997 |
| JP | 10-505910 | 6/1998 |
| JP | 11-512186 | 10/1999 |
| JP | 2000319262 | 11/2000 |
| JP | 20003192362 | 11/2000 |
| JP | 2001041881 | 2/2001 |
| JP | 2001083155 | 3/2001 |
| JP | 2001-253871 | 9/2001 |
| JP | 2004-101409 | 4/2004 |
| JP | 2004-294425 | 10/2004 |
| JP | 2004-305024 | 11/2004 |
| JP | 2004-309303 | 11/2004 |
| JP | 2006053036 A | 2/2006 |
| JP | 2007228905 | 9/2007 |
| RU | 2 141 645 | 11/1999 |
| WO | WO 03/053932 | 7/2003 |
| WO | 2005038442 A1 | 4/2005 |

OTHER PUBLICATIONS

International Search Report and the International Preliminary Report (Form PCT/IB/338) issued for the International Patent Application (PCT/JP2004/002048), which has the same basic application (JP2003-356934) as the present application.

European Search Report of European Patent Appl. No. 04004112.1, which has the same basic application (JP2003-356934) as the present application.

Two Office Actions issued for U.S. Patent No. 7,202,093 (U.S. Appl. No. 10/784,576), which has the same basic application (JP2003-356934) as the present application.

Morio Yashiro et al.—"Preparation and Study of Dinuclear Zinc (II) Complex for the Efficient Hydrolysis of the Phosphodiester Linkage in a Diribonucleotide", Journal of the Chemical Society, Chemical Communications, p. 1793-1794, 1995.

Hidekazu Arii et al.—"A novel diiron complex as a functional model for hemerythrin"—Journal of Inorganic Biochemistry, vol. 82, p. 153-162, 2000.

Harry Adams et al.—"Zinc (II) complexes of tetrapodal ligands derived from tetra-substituted 1, n-diaminoalcohols"—J. Chem. Soc., Dalton Trans., (6) pp. 925-930, 2002.

Kazuya Yamaguchi et al.—"Hydrolysis of phosphodiester with hydroxo- or carboxylate-bridged dinuclear Ni(II) and Cu(II) complexes"—Chem. Commun., (4) pp. 375-376, 2001.

Satoshi Nishino et al.—"Enhanced Nucleophilicity and Depressed Electrophilicity of Peroxide by Zinc (II), Aluminum (III) and Lanthanum (III) Ions"—Journal of Biosciences (2001), 56(½), 138-143.

Junjiro Sato et al.—"Properties of chiral ce (III)—tppn complex as chiral shift reagent in aqueous solution"—Rare Earths, 1998, No. 32, pp. 58-59.

Seikagakujiten (Dictionary of Biochemistry) Tokyo Kagaku Dojin, 1998, the 3rd edition, pp. 1208.

Inamori, K. et al., Detection and Quantification of On-Chip Phosphorylated Peptides by Surface Plasmon Resonance Imaging Techniques Using a Phosphate Capture Molecule, Anal. Chem., 2005, vol. 77, No. 13, pp. 3979-3985.

Kinoshita E. et al., Novel immobilized zinc(II) affinity chromatograph for phosphopeptides and phosphorylated proteins, Journal of Separation Science, 2005, vol. 28, No. 2, pp. 155-162.

Kinoshita E. et al., Phosphate-binding tag, a new tool to visualize phosphorylated proteins, Molecular and Cellular Proteomics, 2006, vol. 5, No. 4, pp. 749-757, Originally published In Press as doi:10.1074/mcp.T500024-MCP200 on Dec. 11, 2005.

Method of Analysis for Chemicals that Promote/Disrupt Cellular Signaling; and, May 2002.

Purification of Phosphorylated Peptides using a Novel Immobilized Metal Affinity Chromatography, 2003.

Matrix-assisted laser desorption/ionization time-of-flight mass spectrometry of phosphorylated compounds using a novel phosphate capture molecule; Hironori Takeda et al., Jul. 2003.

Recognition of phosphate monoester dianion by an alkoxide-bridged dinuclear zinc (II) complex; Eiji Kinoshita et al., Mar. 2004.

* cited by examiner

Incident light      Reflected light

METHOD FOR MEASURING A SURFACE PLASMON RESONANCE AND NOBLE METAL COMPOUND USED FOR THE SAME

FIELD OF THE INVENTION

The present invention relates to a method for measuring a surface plasmon resonance, and a noble metal compound used for the method.

BACKGROUND ART

A certain species of enzymes in living body have serine, threonine, or tyrosine residue in a specific site such as an active center or an allosteric site. The activity of these enzymes is controlled by phosphorylation or dephosphorylation of those hydroxyl groups by enzyme called kinase. In addition, in some enzymes, the activity thereof is controlled by phosphorylation or dephosphorylation of an amino group or an imino group of lysine, arginine, or histidine, or a carboxyl group of aspartic acid or glutamic acid.

As such a metabolic system controlled by phosphorylation-dephosphorylation, known well are control system and decomposition system of glycogenesis. This metabolic system is mainly cascade-controlled and regulated by phosphorylation-dephosphorylation.

In recent years, it has been clear that this phosphorylation-dephosphorylation plays important roles in metabolic systems related to diseases.

For example, abnormalities in phosphorylation-dephosphorylation is assumed to contribute to canceration of cells. That is, progress and interruption of cell cycles are controlled by phosphorylation or dephosphorylation of various enzymes (proteins), cyclin and cyclin-dependent kinase (CDK) participates in this phosphorylation or dephosphorylation. In case where this mechanism is damaged, phosphorylation or dephosphorylation is damaged. As the result, aberrant cell growth is aroused.

It has also been clear that protein kinase C participates in degranulation of histamine leading to allergic diseases such as atopic dermatitis and pollinosis, and that phosphorylated tau protein participates in neurofibrillary tangle generated in brain of Alzheimer disease patient.

In view of the above, understanding of situation of phosphorylation-dephosphorylation of proteins should be useful not only for investigation of genetic expression of living body tissue cell, or evaluation of enzyme activity, but also for diagnosis and medical treatment of diseases.

However, conventionally used methods of determination of phosphorylated or dephosphorylated proteins have various defects.

For example, enzyme immunoassay has advantage that it can analyze a very small amount of subject protein sample, but it is difficult to obtain a sufficient amount of necessary antibodies. In addition, when the molecular weight of a subject protein is not more than several kDa, an antibody binding to a phosphorylated site in protein cannot be prepared.

Additionally, detecting a specific binding of phosphoric acid to protein using phosphoric acid labeled by a radioisotope $^{32}P$ is a possible method. However, handling of radioisotopes deservingly needs special care, and the use of radioisotope requires management and disposal of waste fluid.

Furthermore, since phosphorylated proteins and dephosphorylated proteins have a different electric charge respectively, application of two-dimensional electrophoresis may also be a possible. However, especially in analysis of biological materials, various kinds of proteins included in a sample will make identification of spots very difficult. If radioisotope is used for this spot identification, the above-mentioned problems arise.

In addition to the above-described technologies for determination of phosphorylated or dephosphorylated proteins, a technique using Surface Plasmon Resonance (hereinafter referred to as "SPR") has been developed as general techniques for investigation for compounds such as protein specifically binding to particular compounds such as ligands (refer to FIG. 1). This technique will, hereinafter, be described in detail.

When a light is totally reflected at an interface between materials having different refractive indexes, a light called evanescent wave is generated on a total reflection surface. In addition, a kind of compressional wave of electron generated in a metal-dielectric substance interface called surface plasmon is generated on a surface of a metal. When an angle of incident light is controlled so that phase velocities of both of evanescent wave and surface plasmon may be coincident, this surface resonance will be resonantly excited, and thereby this surface plasmon can significantly increase an electromagnetic field of the surface of the metal. In this case, since energy of the incident light is absorbed by excitation of the surface plasmon, a strength of a reflected light decreases.

A degree of the angle of incidence and a wavelength of incident light giving this absorption exhibit significantly sharp variation according to a state of the surface of the metal, especially within several hundreds nanometers. Accordingly, variation of states such as existence of compounds on a surface of a metal sensitively affects strength of reflected light. When a ligand or the like is bound on the surface of the metal and then a subject sample is subject to the metal, existence of compounds having interaction with the ligands or the like varies the strength of the reflected light. Therefore, when a ligand or the like is supported on the surface of the metal as shown in FIG. 1, and strengths between reflected lights with and without addition of a subject sample is evaluated, a judgment of existence of compounds having interaction with respect to the ligand or the like can be attained. It is also possible to apply the technique to bio-imaging. That is, in cells or living body tissues, this technique will enable an image of localization of a compound having interaction with respect to a specific compound.

In Japanese translation of PCT international publication No. Hei 11-512186, an example of the technique is described. According to the document, when a running buffer→a subject sample→a running buffer are sequentially subject to a noble metal film as shown in FIG. 1, a degree of the angle of incidence giving SPR shows a variation with time as shown in FIG. 2. The technique of the document measures this variation with time, and examines a minimum and maximum value of reflectance, and a relationship between refractive index and period of time. The document also indicates that there can be determined a dissociation constant and a association constant between a compound supported on the noble metal film and a compound in the subject sample, and a concentration of the compound in the sample.

Further, Japanese translation of PCT international publication No. Hei 10-505910 discloses a technique for performing SPR measurement. In the technique, N-(5-amino-1-carboxypentyl)-iminodiacetate is bound to a noble metal film via carboxy methylated dextran, nickel is further coordinated thereto, and SPR is measured. Since this nickel complex shows specific affinity with respect to a peptide having two adjacent histidine residues, it is referred to as His-tag, allowing detection of a peptide having dihistidine residue in a subject sample.

In addition, for measuring a surface plasmon resonance, application of Raman spectroscopy is a possible. Raman spectroscopy is a technique of obtaining information on compounds, wherein, in a scattered light generated by irradiation of a monochromatic light with a fixed frequency $v_0$ to a material, a scattered light (Raman scattering light) ($v_0 \pm v_i$) other than a same frequency is measured. In detail, since this Raman frequency $v_i$ is equal to a frequency between levels of vibration or energy of rotation of a molecule or a crystal constituting the material, this provides sources of information for determination, identification, and quantification of energy levels of the material (refer to "Dictionary for Chemistry (Kagaku Daijiten)" Tokyo Kagaku Dojin).

However, since this Raman scattering light is very weak, its measurement has been conventionally carried out by enhancing the light using the surface plasmon resonance effect (for example, publication of unexamined patent application No. Hei 9-257578). Although light does not couple with electron wave (plasmon) in general, it can couple on a metallic particle surface. Then, the technique enhances the weak Raman band strength with a metal existing in close proximity to a specimen to be measured.

However, the enhancing effect of Raman band strength by the conventional technology was not necessarily satisfactory. The reason is that all target molecules are not forced to contact metal even when a substrate (metal) 2 and a sample 3 were made to exist close to each other as in FIG. 1 of No. Hei 9-257578, although a smaller distance between a target molecule and a metal gives a higher surface plasmon resonance effect. A same circumstance is observed when the metal is added in an aqueous solution sample.

By the way, Hironori Takeda et al., RAPID COMMUNICATIONS IN MASSSPECTROMETRY, Vol. 17, Issue 18, pp. 2075-2081 (2003), describes a method for determining a molecular weight of a phosphorylated compound using a compound specifically bound to a phosphate group, that is phosphoric acid monoester group. However, the document provides neither description nor suggestion for a technical idea of making a metal approach a target compound via this specific binding compound, or for an idea of applying the compound to measurement of a surface plasmon resonance.

SUMMARY OF THE INVENTION

Under the above-described situation, it is an object of the present invention to provide a method for measuring a surface plasmon resonance for detection of a phosphorylated peptide (protein) in a subject sample, and for judgment whether a peptide is phosphorylated or not. It is also object of the present invention to provide a noble metal compound, usable for the method, having substituent groups (Phos-tag) with specific and high coordination capability on a phosphoric acid monoester group.

In addition, it is another object of the present invention to provide a precursor compound for producing a noble metal compound having the Phos-tags on a surface thereof as substituent groups.

In order to solve the problems described above, the present inventors devoted themselves to research for a metal complex capable of being coordinated to a phosphate group (phosphoric acid monoester group) bound to a protein, and have found out that a substituent group of the present invention has an extremely high capability of coordination to two hydroxyl groups in a phosphoric acid ion or in a phosphoric acid monoester, as a result, the substituent group can form a binding to a peptide or strongly coordinates to a phosphate group (phosphoric acid monoester group), and it can specifically bind to a phosphorylated peptide to form a composite even in a mixed sample including a plurality of peptides. Thereby, the present inventors found out that measurement of SPR using this substituent group can solve the above described problems, leading to completion of the present invention.

The first method for measuring a surface plasmon resonance of the present invention comprises:

placing a noble metal compound on a bottom face of a prism, irradiating a light to the prism to detect a reflected light, wherein, the noble metal compound has substituents of following formula (I) on a side opposite to a side contacting the prism, and a subject sample is added to a side having the substituent groups (I) in the noble metal compound.

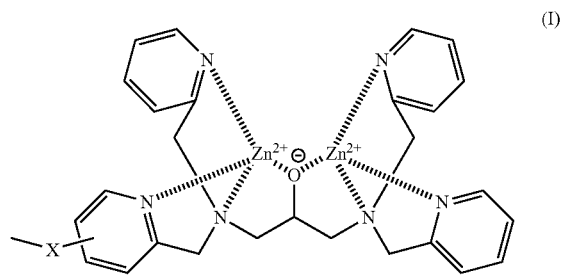

(I)

[wherein, X represents a linker group]

In addition, the second method for measuring surface plasmon resonance of the present invention comprises:

adding a noble metal compound having substituents of the above formula (I) on a surface thereof to a subject sample, and using Raman spectroscopy.

A noble metal compound of the present invention is used for the above method for measuring a surface plasmon resonance, and has the substituent groups represented with the formula (I) on the surface thereof. When the noble metal compound is used by the first method, it preferably has a film-shape, and when it is used by the second method, it preferably has a particle-shape.

A precursor compound as a producing precursor of the noble metal compound is easily transformable into the noble metal compound by treating with zinc metal salts or the like, and it has substituent groups represented with formula (VII) on a surface of a noble metal. Since a form of the precursor compound is determined according to the form of the noble metal compound as a producing targeted compound, it preferably has a metallic film-shape or a metallic particle-shape.

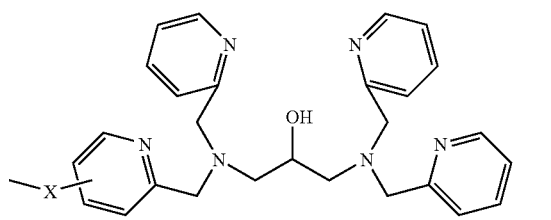

(VII)

[wherein, X represents a linker group]

BEST MODE FOR CARRYING OUT THE INVENTION

Hereinafter, a measuring method of an SPR of the present invention will be described first.

Measurement of an SPR in the first method of the present invention can be carried out using publicly known devices. For example, a device described in U.S. Pat. No. 5,313,264 specification can be used. This SPR measuring method is extremely suitable for detection of a phosphorylated peptide, based on advantages that:

(1) a labeling operation such as introduction of fluorescence coloring group is unnecessary,
(2) the method has a high sensitivity with respect to molecules with a comparatively high molecular weight, and
(3) easy bond formation of molecules having a thiol group or a disulfide group to a surface of a noble metal compound such as gold enables introduction of substituent groups onto the surface with a high density.

Figure 1:
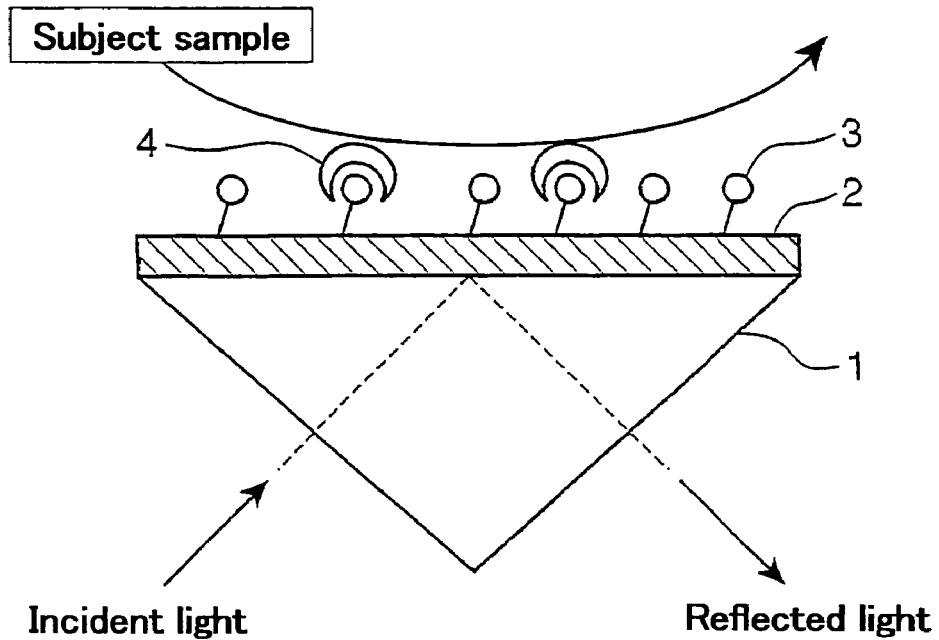
FIG. 1 schematically illustrates one procedure for measuring an SPR. After adjustment of a wavelength of an incident light and an incident angle for measurement of an SPR, that is for decrease of a reflected light intensity, a subject sample is added to the noble metal film having a bound ligand, and a variation of the incident light strength is to be observed. In the Figure, a reference numeral 1 represents a prism, 2 represents a noble metal film, 3 represents a ligand, and 4 represents a protein included in a subject sample which interacts with the ligand.
Figure 2:
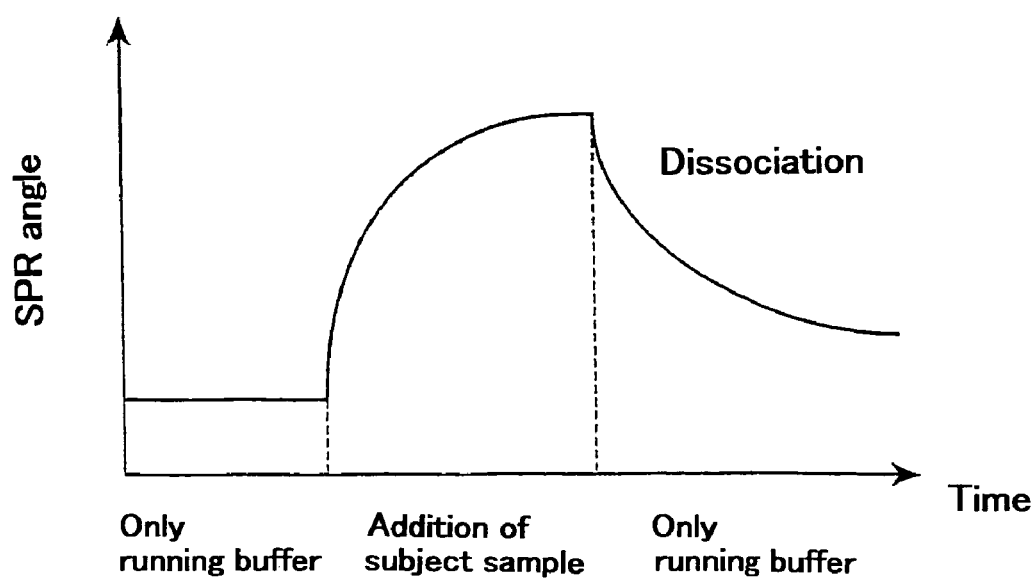
FIG. 2 schematically illustrates a variation with time of an SPR angle in continuous application in order of a running buffer→a subject sample→a running buffer, in SPR measurement given in FIG. 1. This illustrates that binding of a compound in a subject sample to a noble metal film gives variation in an incident angle in an SPR measurement.

The measurement principle has already described above using FIGS. 1 and 2, and descriptions with respect to the SPR measuring apparatus will, hereinafter, be concretely given. In FIG. 1, when a light is irradiated to a noble metal film from a prism side so that a total reflection is given, a reflected light intensity will drop at a certain angle based on generation of an SPR. Since this angle varies sharply based on a variation of an amount of a compound bound, i.e. a variation of a mass, to the noble metal film, the SPR measuring apparatus can display this mass variation as a measurement data (Resonance Unit, 1 RU=1 pg/mm$^2$) from a strength of the reflected light.

Therefore, after introduction of substituent groups exhibiting specific binding affinity with respect to a phosphorylated peptide to the noble metal film, a subject sample is subject to the film to obtain a data. Then, comparison between the obtained data and a data in a steady state enables understanding of existence or an amount of the phosphorylated peptide in the subject sample.

The second method of the present invention can directly use conventional devices for Raman spectroscopy. However, it is necessary to make the noble metal compound (noble metals particles) of the present invention subject to a subject sample. As a result, not only a peak of a phosphorylated peptide shifts but also a strength of the peak is intensified by a surface plasmon resonance effect based on binding of the noble metal compound, as compared to a case without action of the noble metal compound of the present invention. Thus, comparison of the data with a data of Raman spectrum in a case without noble metal compound action of the present invention enables judgment whether the peptide is phosphorylated or not.

A subject sample used by the second method of the present invention has a form of an aqueous solution or an aqueous dispersion. The reason is that a noble metal compound of the present invention is to be bound to a phosphorylated peptide. The subject sample may, for example, be untreated biological materials, and it is preferably a sample obtained by purifying a peptide to be judged of existence of phosphorylation. This is because that a satisfactory spectrum may not be obtained by existence of impurities in Raman spectroscopy.

A substituent group used with the noble metal compound of the present invention is extremely excellent in specific binding ability to a phosphorylated peptide, and has following structures:

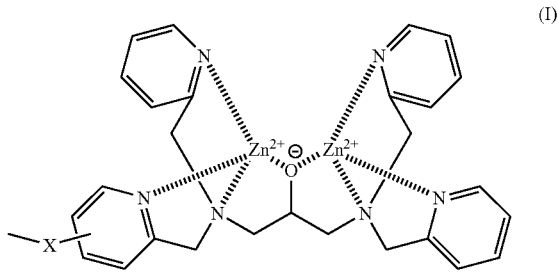

(I)

[wherein, X represents a linker group]

A reason for having selected Zn as a coordinative metal in the formula (I) is that it has an extremely high coordination capability to a phosphate group (phosphoric acid monoester group) of a phosphorylated protein.

In the noble metal compound of the present invention, "linker group" represents a group for bonding a noble metal portion and the above principal skeleton, that is a main part having interaction to a phosphorylated protein, hereinafter referred to as "Phos-tag". The linker group has functions for enabling easy producing of the noble metal compound of the present invention, and for increasing of degree of freedom of the substituent group (I) to realize easy coordination to a phosphate group bound with the peptide.

The kind of "linker group" is not especially limited as long as it has the above-mentioned function, and it includes, for example: sugar chain, $C_1$-$C_6$ alkylene group, amino group (—NH—), ether group (—O—), thioether group (—S—), carbonyl group (—C(=O)—), thionyl group (—C(=S)—) ester group, amido group, urea group (—NHC(=O)NH—), thiourea group (—NHC(=S)NH—), biotin-streptavidin complex, biotin-avidin complex; a sugar chain having, at an end thereof, a group selected from a group consisting of amino group, ether group, thioether group, carbonyl group, thionyl group, ester group, amido group, urea group, thiourea group; and $C_1$-$C_6$ alkylene group having, at an end thereof, a group selected from a group consisting of amino group, ether group, thioether group, carbonyl group, thionyl group, ester group, amido group, urea group, thiourea group, biotin-streptavidin complex, biotin-avidin complex; $C_1$-$C_6$ alkylene group having, at both ends thereof, groups identical to each other or different from each other selected from a group consisting of amino group, ether group, thioether group, carbonyl group, thionyl group, ester group, amido group, urea group, thiourea group; and a group obtained by linearly bonded two or more groups selected from a group consisting of the above-mentioned groups.

An end group on a side bound to a noble metal portion of the linker group is preferably a thioether group. This is because that this noble metal compound can be easily produced using a thiol compound or a disulfide compound.

In the present invention, "sugar chain" indicates a common saccharide bonded linear or branched, and for example, a dextran obtained by polymerization by glycoside linkage of D-glucose may be exemplified. In addition to a function of the above-described linker group, this sugar chain has high hydrophilicity and excellent affinity with biological materials. Further, since this sugar chain having a branched chain can be easily synthesized, a larger number of principal skeletons of the substituent group (I) may advantageously be bonded.

Here, "$C_1$-$C_6$ alkylene group" represents a linear or branched divalent aliphatic hydrocarbon group with a carbon number of 1 to 6, and includes for example methylene, ethylene, propylene, tetramethylene, hexamethylene, methylethylene, methylpropylene, dimethylpropylene, and the like. $C_1$-$C_4$ alkylene group is preferable and $C_1$-$C_2$ alkylene group is more preferable.

A length of the above-described linker group is not especially limited, and it is preferably not more than 200 nm, and more preferably not more than 100 nm. This is because that a linker group having a smaller length enables sharper detection of a phosphorylated peptide.

To a pyridine ring of the substituent group (I), a methyl group or the like may possibly be introduced as long as the resulting substituent group has the same functional effect to the substituent group (I). Such an equivalent shall also be included within the scope of the present invention.

In addition, a position of the linker group in the substituent group (I) of the present invention is not especially limited, and the linker group may exist in a position illustrated by following substituent group (I').

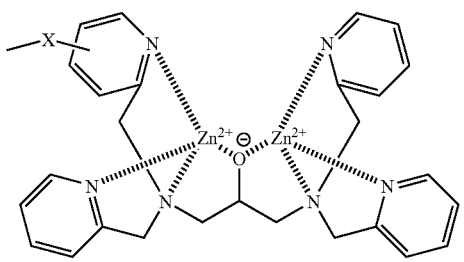

(I')

The substituent group (I') and substituent group (I) are completely equivalent to each other, and it is not necessarily clear which substituent group may be obtained in synthesis reaction. It is probable that they are obtained in a mixture state in fact, and naturally the substituent group (I') shall also be included within the scope of the present invention.

In the present invention, "noble metals" represents gold, silver, platinum, rhodium, ruthenium, palladium, osmium, or iridium. In the present invention, any of gold, silver, platinum, or rhodium are preferably used, and gold is especially preferably used. The reason is that gold is proven to demonstrate satisfactory surface plasmon resonance effect.

In the first method, a film form is preferable as a form of the noble metal compound of the present invention. The reason is that a film form materials can be applicable to a measuring apparatus of the surface plasmon without any treatment. A thickness of this noble metal film is not especially limited, and it is preferably 10 to 100 nm, and usually approximately 50 nm.

In the second method, a particle form is preferable. The reason is that since the present invention makes the noble metal compound bind to a phosphorylated peptide included in a subject sample dissolved or dispersed therein, the noble metal compound is necessarily to be dispersed in the subject sample. A mean particle size of the particle is preferably within a range of 30 to 50 nm. A particle diameter less than 30 nm may not sometimes give sufficient enhancement effect of Raman scattering light, and a particle diameter more than 50 nm gives possible excessive aggregation of the particles during measurement. However, since the range represents a mean particle size, particles outside the range may exist.

Measuring methods of the mean particle size is not especially limited. Since particle sizes to be measured are probably in a range of several nm to tens of nm, a particle size distribution may be measured with a device applicable for a laser scattering-method being suitable for particle diameter measurement of micro-particles (laser scattering photometer), and an average of particle diameter may be calculated.

Although the noble metal compound of the present invention may easily be produced by a method including scheme 1, a production method is not limited to methods illustrated hereinafter.

[Scheme 1]

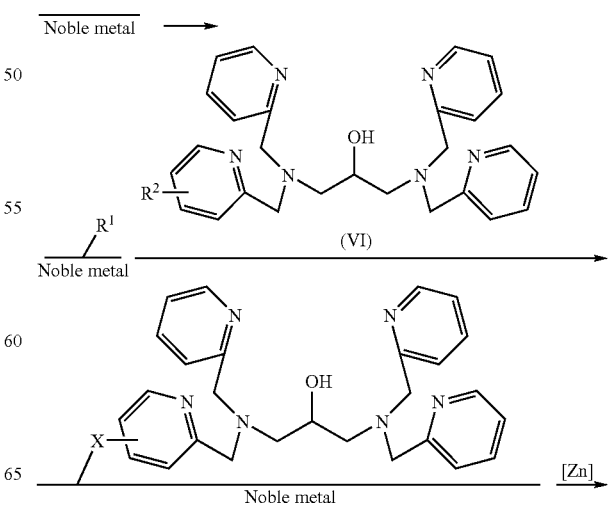

-continued

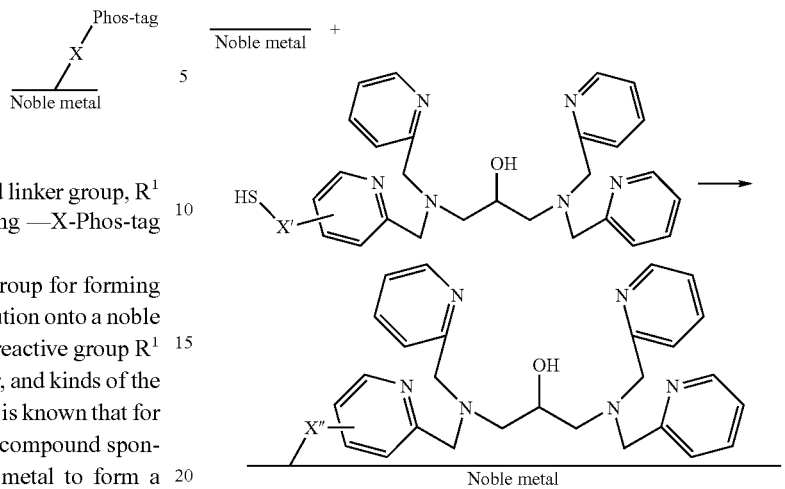

[wherein, X represents the above-mentioned linker group, $R^1$ and $R^2$ represent reactive groups for forming —X-Phos-tag group on a surface of the noble metal film.]

In the scheme 1, firstly $R^1$ as a reactive group for forming a linker group X is made to apply by substitution onto a noble metal. Here, kinds of bonding between the reactive group $R^1$ and the noble metal are not necessarily clear, and kinds of the bonding shall especially not be discussed. It is known that for example, a thiol compound and a disulfide compound spontaneously adsorb to a surface of a noble metal to form a monomolecular film called a self-assembled monolayer. Therefore, when a bonding between the reactive group $R^1$ and the noble metal through a sulfur atom exists, kinds of bonding between the noble metal and the sulfur atom in the above scheme is not especially limited, and they should just be bonded by a certain interaction.

When a final targeted compound is a noble metal film, the noble metal film to be substituted with the reactive group $R^1$ should just be cut into a suitable form for SPR measuring apparatus to be used, after a noble metal material is ductiled to a suitable thickness. When the final targeted compound is a particle, after producing the particle using publicly known metallic particle production methods, excessively small or excessively large particles should just be removed using a membrane filter or the like corresponding to a desired particle diameter.

In the scheme 1, it has been clear that when the reactive group $R^1$ is made to bond with the noble metal surface via the sulfur atom, a reaction between a thiol compound (for example, $R^1$—SH) and the noble metal advances extremely easily, and reaction conditions or the like should just follow conventional methods. For example, only contacting of the noble metal surface with a solution of a thiol compound can start condensation between them.

Subsequently, in order to bond a Phos-tag precursor via the linker group X, made to react is tetrakis(pyridine-2-ylmethyl)-1,3-diaminopropane-2-ol derivative (compound (VI)) having a substituent group $R^2$. In the scheme 1, kinds of $R^1$ and $R^2$, solvents, reaction temperatures, other reagents, refining methods, or the like in a process of reaction of $R^1$ and $R^2$ are primarily determined by a kind of X. For example, when $R^1$ and $R^2$ are to be bonded with an amido bond to obtain the X, a pair of a group having an amino group (primary amino group) and an activated carboxy group may be exemplified as a pair of $R^1$ and $R^2$. As reaction conditions in this case, general conditions in synthetic organic chemistry field should just be applied. In this way, a noble metal compound having substituent groups (VII) on a surface may be obtained.

In addition, noble metal compounds having the substituent groups (VII) may also be produced by following methods.

[wherein, X" represents a group having a sulfur atom on a side of the noble metal among the above-mentioned linker groups, and X' represents portions other than the end sulfur atom among X" (when X" is only a sulfur atom, X' is simply represents a covalent bond.)]

Since the reaction of the thiol compound and the noble metal advances extremely easily as mentioned above, the tetrakis(pyridine-2-ylmethyl)-1,3-diaminopropane-2-ol derivative substituted by a group having a thiol group at an end thereof allows synthesis of a precursor compound of the noble metal compound having Phos-tags on a surface thereof.

Finally, addition of a metal salt to the noble metal compound having substituent group (VII) gives a noble metal compound having Phos-tags on a surface thereof. For example, zinc nitrate (II) or zinc acetate (II) may be added in this case, and in case of addition of zinc acetate (II), a following compound having acetic acid coordinated thereto is once obtained.

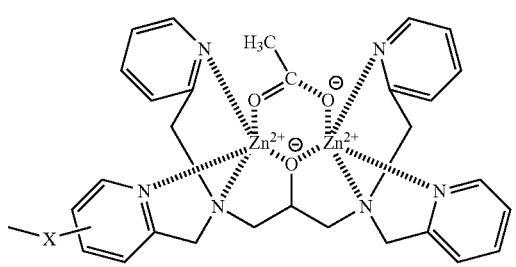

This compound is more stable than the substituent group (I), and may conveniently be preserved. This compound is equivalent to the substituent group (I), and can be used in a same manner as the substituent group (I). That is, since a phosphoric acid monoester group exchangeably coordinates to the acetic acid in SPR measurement, phosphorylated peptides can be detected.

A raw material compound (compound (VI)) in the scheme 1 for bonding the Phos-tags to the noble metal may be produced by a following scheme 2.

[Scheme 2]

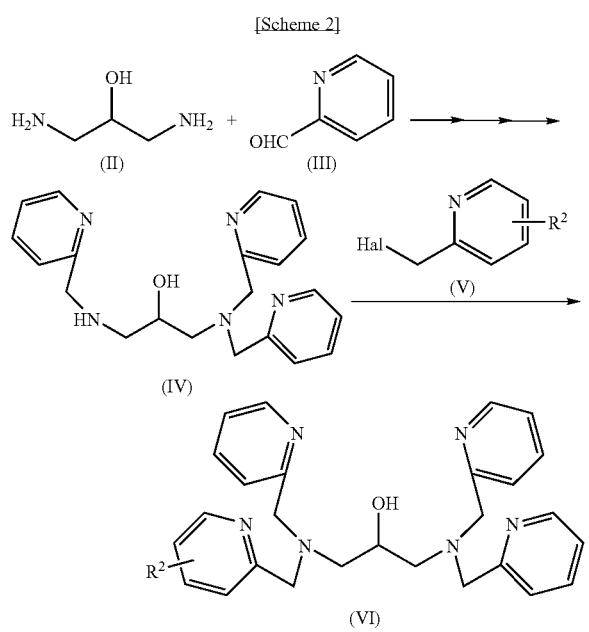

[wherein, $R^2$ represents the same definition as mentioned above. "Hal" represents a halogen atom and preferably represents bromine atom.]

Compound (II) (1,3-diamino-2-propanol) as a raw material compound is commercially available. In addition, since compound (III) and compound (V) have comparatively simple structures, they are commercially available, or they may be synthesized by conventionally known methods to those skilled in the art.

In the scheme 2, the compound (IV) is first obtained by a condensation reaction of the compound (II) and (III) in the presence of a catalyst. Although sequential introduction of the compound (III) is possible in this reaction, use of the compound (III) in an amount of 3-equivalent or more enables synthesis of the compound (IV) at an one-step reaction.

In the scheme 2, is carried out a reductive amination reaction as a condensation reaction. In the case, as a solvent to be used, any solvents may be used without special limitation as long as the solvent may substantially dissolve compound (II) and (III) and not inhibit the reaction. For example, alcohols such as methanol, ethanol, and isopropanol; ethers such as diethylether, tetrahydrofuran, and dioxane; water; and mixtures of the above-mentioned solvents may be used.

In the reductive amination reaction, after condensation of compound (II) and (III) in the presence of concentrated hydrochloric acid as a catalyst, a reduction is carried out by a common reductive reagent.

As a reaction temperature and a reaction temperature, preferable conditions may just be used based on a kind of raw material compounds or the like. For example, the reaction is to be carried out at a temperature of 20 to 80° C., and in a period of 12 to 100 hours.

After completion of the reaction, solvent and the like are evaporated off in vacuo, and then water is added to the reaction mixture. Subsequently, after extraction with a non-aqueous solvent, an organic phase obtained is dried with anhydrous magnesium sulfate or the like, and the solvent used is evaporated off in vacuo. Next, a residue obtained is purified by conventionally known methods such as silica gel column chromatography to give the compound (IV).

Production method of compound (IV) is not limited to the method represented by the scheme 2, and for example, the compound (IV) may also be synthesized from the compound (II) and halogenated compounds.

A subsequent reaction with the compound (V) may give the compound (VI). As this reaction, a synthetic reaction of common tertiary amine is employable. For example, a condensation reaction in the presence of bases in solvents may be employable. In addition, introduction of protective group and cleaving of the protective group may be appropriately carried out according to a kind of $R^2$ in the step. Or the compound (VI) may be synthesized by exchanging the inactive substituent group into $R^2$ by a conversion of a functional group, after the step using a compound having inactive substituent group instead of $R^2$ in the compound (V). For example, after the step using a compound having a nitro group as an inactive substituent group, the nitro group may be converted into an amino group as a reactive group.

As a substituent group that can be used for the method of the present invention, a following complex compound (VIII) may also be used instead of the substituent group (I).

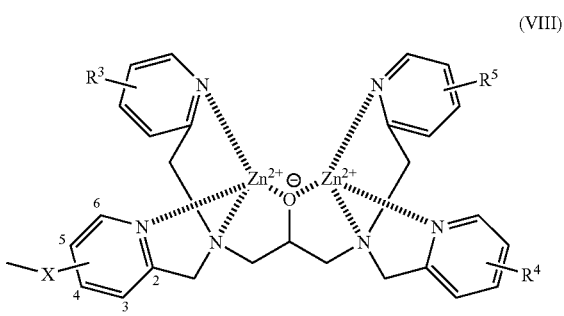

[wherein, X represents a same definition as mentioned above. $R^3$ to $R^5$ represent a electron-donative substituent group in 4-position or 6-position on a pyridine ring.]

The substituent group (VIII) used in a method of the present invention has pyridine nitrogen in an electrically rich state by a electron-donative substituent group introduced into a suitable substituted position, and therefore it has outstanding coordination property with respect to zinc, giving easier productivity and stability. This substituent group may be used as pursuant to substituent group (I).

Although the present invention will, hereinafter, be described in detail with reference to Production Examples and Test Examples, the scope of the present invention is not limited to them.

EXAMPLE

Production Example 1

Production of Phos-Tag Sensor Chip for SPR Analysis

A sensor chip (produced by BIOCRE, Sensor Chip CM5) coated with carboxymethyldextran was set in an SPR measuring apparatus (produced by BIOCRE, BIOCORE J).

As a running buffer, used was 10 mM of HEPES, 2-[4-(2-hydroxy-ethyl)-1-piperazinyl]ethanesulfonic acid,—sodium hydroxide aqueous solution (pH 7.4) including $5 \times 10^{-3}\%$ (V/V) of Tween 20, 0.20 M of sodium nitrate, and 10 μM of zinc nitrate. A temperature of a sensor chip was set at 25° C., and a rate of flow of the running buffer was set at 30 μL/min. After check of a stable value of a surface plasmon resonance, an aqueous solution mixture of EDC (1-ethyl-3,4-dimethylaminopropylcarbodiimide, 200 mM) as a carboxyl group activator and NHS (N-hydroxysuccinimide, 50 mM) was added over 6 minutes to activate a carboxyl group of the sensor chip.

Next, in order to support Phos-tags on the sensor chip, 50% (v/v) acetonitrile solution (10 mM) of N,N,N'-tri(2-pyridyl-methyl)-N'-[5-N"-(2-aminoethyl)carbamoyl-2-pyridylm-ethyl]-1,3-diamino-propane-2-ol was added over 6 minutes. Subsequently, in order to block remaining activated carboxyl groups, 1.0 M monoethanolamine aqueous solution was added over 6 minutes.

By the above operation, a sample channel, that is flow cell A, having a sensor section with the Phos-tags bound thereto was prepared.

Comparative Production Example 1

A sample channel, that is flow cell B, having a reference section without the Phos-tag bound thereto was produced in parallel with the flow cell A, using a similar procedure to the above Producing Example 1 including activation of the carboxyl group and block thereof, except for a Phos-tag was not supported.

Test Example 1

As analytical samples, used were (i) β-casein (penta phosphorylated protein, produced by SIGMA), (ii) dephosphory-lated β-casein, and (iii) bovine serum albumin (BSA, produced by New England BioLabs). The dephosphorylated β-casein was prepared by incubating a mixed solution of β-casein 10 mg/mL (50 μL), acid phosphatase from potato (SIGMA), and 0.20 M MES-NaOH (pH 6.8, 50 μL), at 38° C. for 12 hours. Each sample was dissolved in the running buffer used in Production Example 1 to obtain a sample solution with a sample concentration of 1.5 μM.

An SPR measurement was carried out for the sample solution. In detail, the flow cells A and B prepared in Production Example 1 and Comparative Production Example 1 are respectively stabilized by running buffer. Each sample solution was flowed in the cells at a temperature of 25° C. and at a rate of flow of 30 μL/min, and association was carried out for 15 minutes. Next, only the running buffer was flowed for 15 minutes for dissociation. After measurement for each sample solution, flowed were 25 mM monopotassium phosphate—25 mM disodium phosphate aqueous solution (pH 6.86) for 6 minutes, 0.20 M disodium ethylenediaminetet-raacetate aqueous solution (pH 7.4) for 6 minutes, and the running buffer for 5 minutes to reactivate the sensor chip, that is, to remove residual bonded matter.

Figure 3:
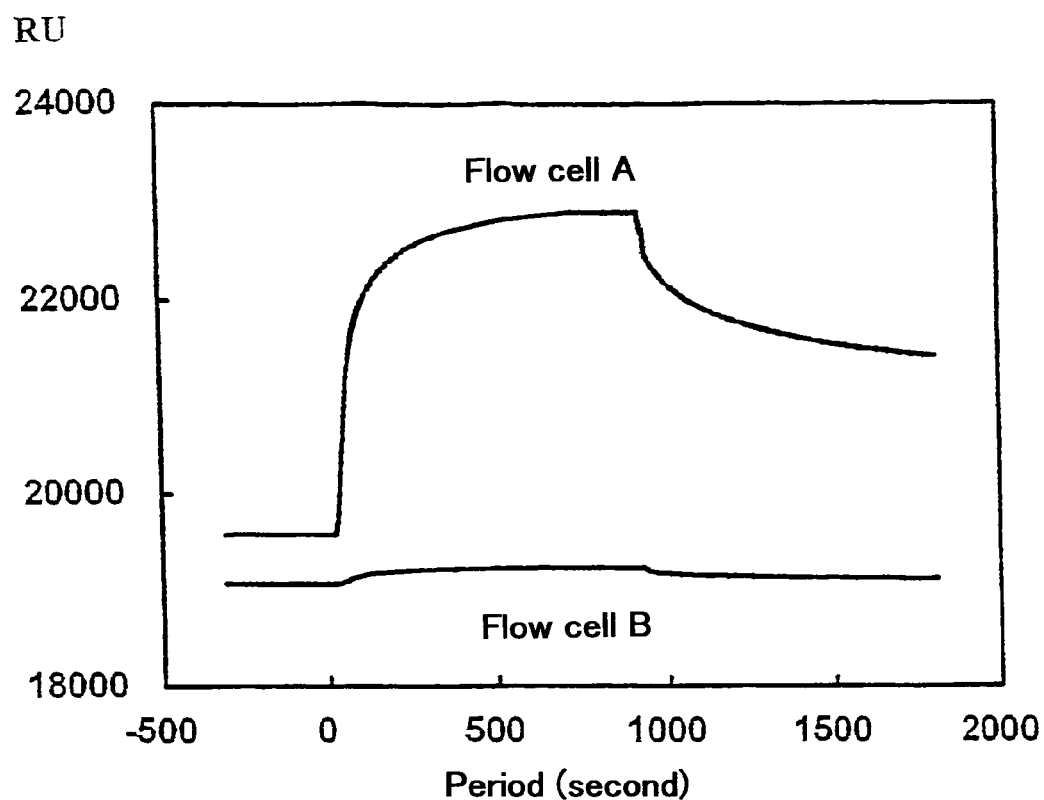
FIG. 3 illustrates a result of an SPR measurement about a sample including phosphorylated β-casein.
Figure 4:
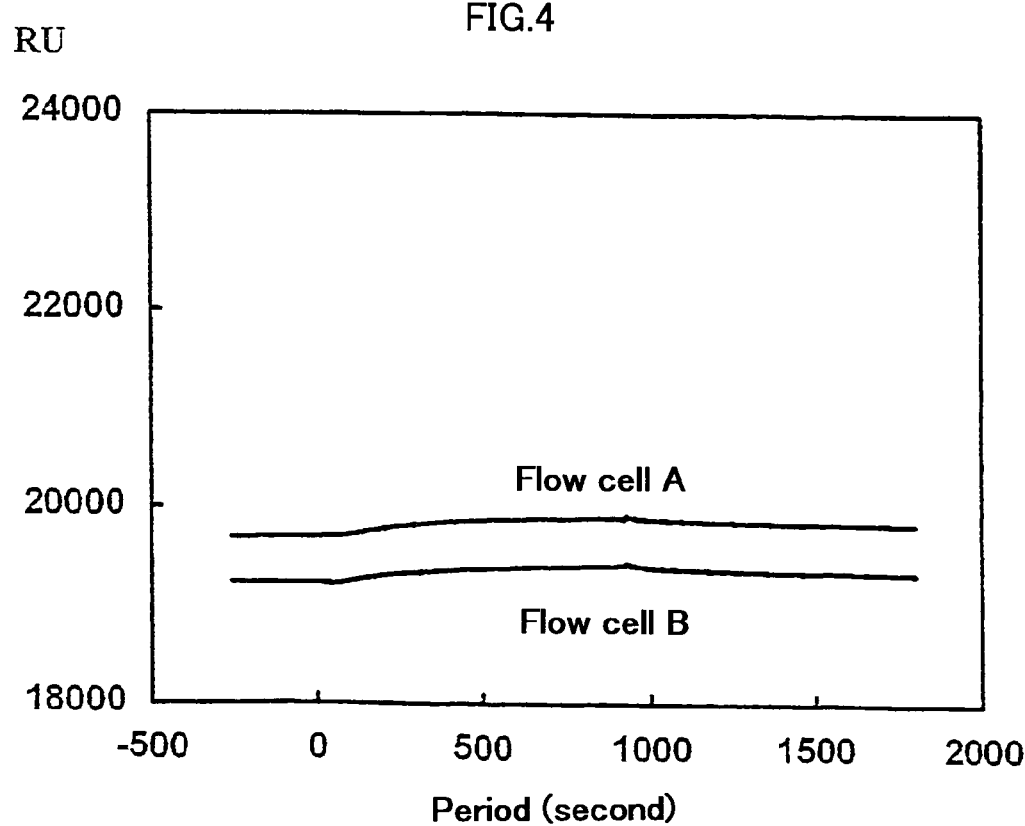
FIG. 4 illustrates a result of an SPR measurement about a sample including dephosphorylated β-casein.
Figure 5:
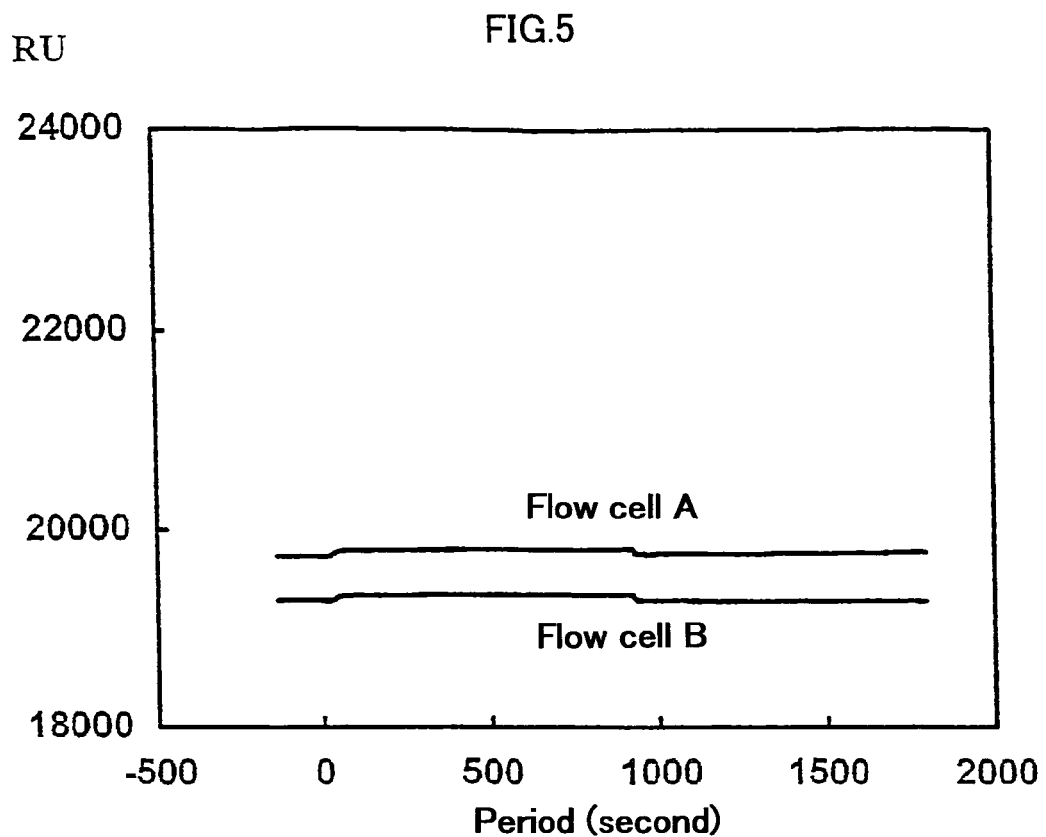
FIG. 5 illustrates a result of an SPR measurement about a sample including a non-phosphorylated bovine serum albumin (BSA) as a common protein.
Figure 6:
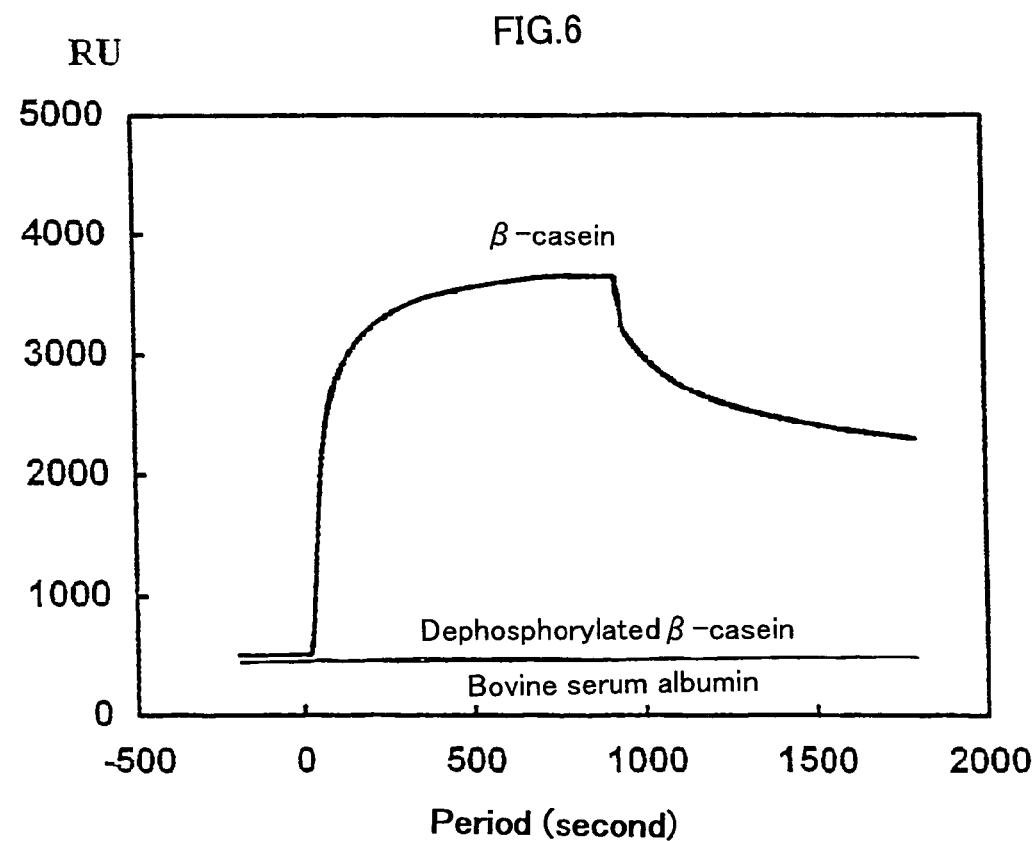
FIG. 6 illustrates differences obtained by subtracting RU values of a flow cell B from RU values of a flow cell A in test results illustrated in FIG. 3 to 5.

FIGS. 3 to 5 show each SPR test result of respective samples (i) to (iii), and FIG. 6 shows a difference obtained by subtracting the RU value of flow cell B from the RU value of flow cell A in the test result of each sample. According to the results of FIGS. 4 to 6, variation of flow cells A and B is almost same, showing that dephosphorylated β-casein and BSA do not give a specific bonding. On the other hand, the results of FIGS. 3 and 6 clarified that phosphorylated β-casein makes specific binding to the sensor part having Phos-tags bound thereto (amount of the maximum binding=3150 RU). Therefore, it was proved that a method according to the present invention can detect only phosphorylated peptide.

Test Example 2

As analytical samples, (iv) phosphorylated SRC peptide (monophosphorylated peptide, produced by ANA SPEC Inc.) and (v) SRC peptide (non-phosphorylated peptide, produced by ANA SPEC Inc.) were used. Each sample was dissolved in the running buffer used in Production Example 1 to obtain sample solutions with sample concentrations of 1 to 15 μM.

Figure 7:
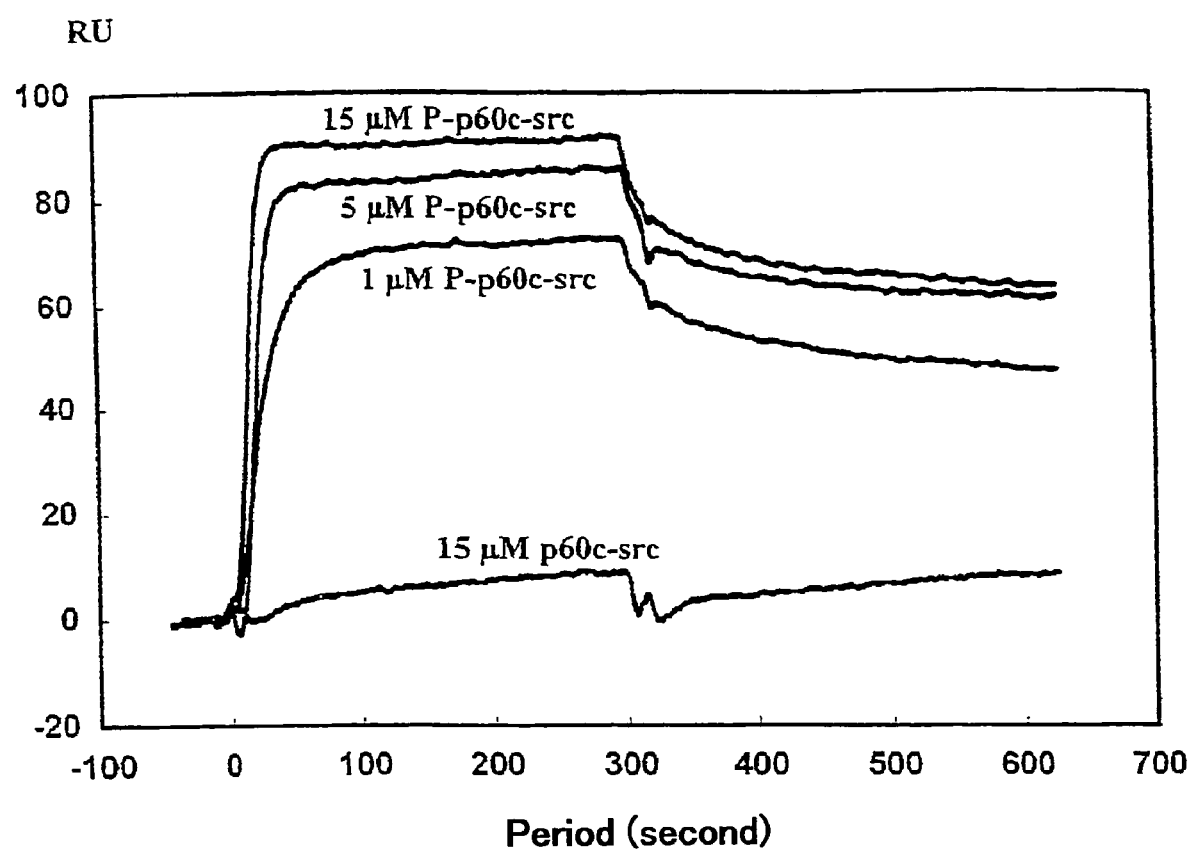
FIG. 7 illustrates a result of SPR measurements about samples including a phosphorylated peptide (P-p60csrc) or a non-phosphorylated peptide (p60csrc).

SPR measurement for the sample solutions was carried out using the flow cells A and B produced in Production Example 1 and Comparative Production Example 1. In detail, SPR measurement was carried out under the same conditions as in Test example 1, except that association and dissociation of the samples were carried out for 5 minutes, respectively, and reactivation of the sensor chip (removing of residual bonded matter) was carried out with 0.40 M phosphate buffer (pH 7.0) for 5 minutes, with 0.20 M disodium ethylenediaminetetraac-etate aqueous solution (pH 7.4) for 5 minutes, and with the running buffer of the Production Example 1 for 5 minutes in the Test example 1. FIG. 7 shows the results.

The result shows that the non-phosphorylated peptide hardly showed a variation even at a concentration of 15 μM. On the other hand, the result shows that the phosphorylated peptide enabled clear recognition of the existence thereof not only at a concentration of 15 μM but also at concentrations of 1 and 5 μM. Therefore, it is clearly proved that the existence of bonding of phosphoric acid can clearly be determined in peptides having an identical amino acid sequence by the present invention.

Production Example 2

Production of Phos-Tag Sensor Chip for SPR Analysis

A streptavidin sensor chip having streptavidin bound on a surface thereof (produced by BIOCRE, Sensor Chip SA) was set to an SPR measuring apparatus (produced by BIOCRE., BIOCORE J).

As a running buffer, used was 10 mM HEPES, 2-[4-(2-hydroxyethyl)-1-piperazinyl]ethanesulfonate,—sodium hydroxide aqueous solution (pH 7.4) including 5×10⁻³% (v/v) Tween 20, 0.20 M sodium nitrate, and 10 μM zinc nitrate. A temperature of the sensor chip was set at 25° C., and the Running buffer was flowed at a rate of flow of 30 μL/min until a value of a surface plasmon resonance showed stabilized state.

Then, in order to make the Phos-tag to be support to the sensor chip, flowed was a running buffer solution of 1.0 mM of N,N,N' tri(2-pyridylmethyl)-N'-[5-N"-2-(6-D-biotinami-dohexacarboxy-amideethyl)carbamoyl-2-pyridylmethyl]-1, 3-diaminopropane-2-ol having a biotin structure at an end thereof, a compound having following structure. Conditions used were: a temperature of 25° C., a rate of flow of 30 μL/min, and a period for association of 6 minutes.

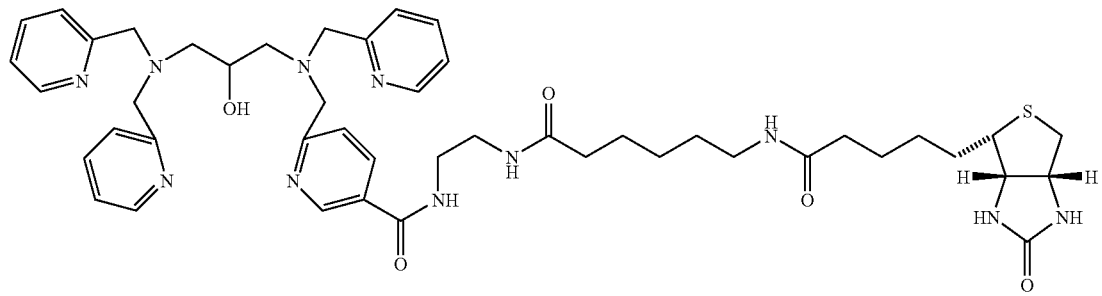

Since the above compound was coordinated to zinc ion in the running buffer to form a Phos-tag, and the biotin at the end showed extremely high affinity for streptavidin, the Phos-tags would be supported on the sensor chip.

Comparative Production Example 2

A sensor chip devoid of a Phos-tag bound thereto was produced using a similar procedure to Production Example 2 except that a Phos-tag was not supported.

Test Example 3

As an analysis sample, used was a β-casein (penta phosphorylated protein, SIGMA) dissolved in a running buffer which is a 10 mM HEPES—sodium hydroxide aqueous solution (pH 7.4) including $5 \times 10^{-3}\%$ (v/v) of Tween 20, 0.20 M sodium nitrate, and 10 μM zinc nitrate. A sample concentration was set to 1.5 μM.

An SPR measurement for the analysis sample was carried out under conditions of a temperature of 25° C., a rate of flow of 30 μL/min, a period for association of 15 minutes, and a period for dissociation of 10 minutes. After measurement, flowed were 0.40 M phosphorate aqueous solution for 6 minutes, 0.20 M disodium ethylenediaminetetraacetate aqueous solution (pH 8.0) for 6 minutes, and the running buffer for 5 minutes to reactivate the sensor chip, that is, to remove residual bonded matter.

Figure 8:
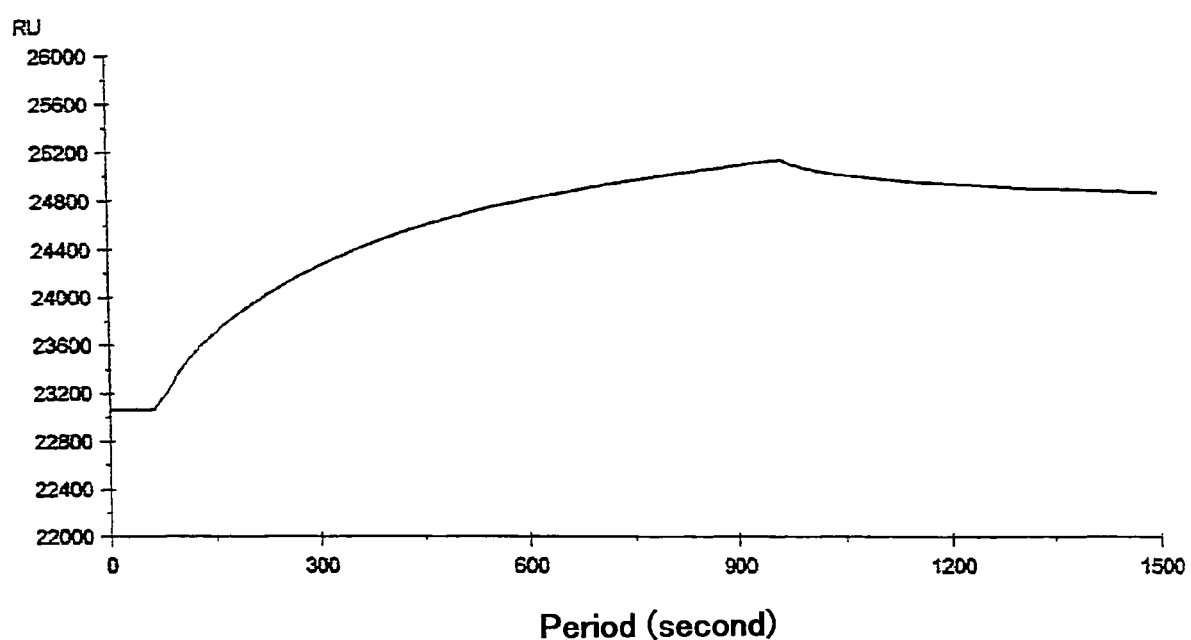
FIG. 8 illustrates a result of SPR measurements about a sample including a phosphorylated β-casein.

FIG. 8 shows the test result. The result shows that the RU value increased by 2056 due to flow of the analysis sample, enabling identification of binding of the phosphorylated protein to the noble metal film of the present invention, that is noble metal sensor chip having Phos-tags bonded thereto. In addition, an experiment conducted under identical conditions as described above using a bovine serum albumin as a non-phosphorylated protein instead of the phosphorylated protein failed to give no variation of RU value. Therefore, it was clearly shown that the noble metal film of the present invention enabled detection of only protein having phosphoric acid bound thereto.

In addition, an experiment carried out under identical conditions using the sensor chip produced by Comparative Production Example 2 gave no variation of RU value.

INDUSTRIAL APPLICABILITY

A method for measuring a surface plasmon resonance (SPR) of the present invention allows determination of the existence of a phosphorylated peptide (protein) even in a subject sample such as biological materials including a variety of compounds. In addition, the method should also determine an amount and a concentration of the phosphorylated peptide. Furthermore, the method can also determine whether the peptide is phosphorylated or not. Therefore, application of a method of the present invention to biological materials or the like is very useful in terms of possibility of application to diagnosis of diseases.

Furthermore, since a noble metal compound of the present invention exhibits superior coordinate bonding property to a phosphorylated peptide compared to any conventional noble metals, the noble metal compound is useful as a material usable in the above described methods. The precursor compound is also useful.

The invention claimed is:

1. A method for measuring a surface plasmon resonance, comprising:
   placing a noble metal compound on a bottom face of a prism,
   irradiating a light to the prism to detect a reflected light for detecting a phosphorylated peptide in a subject sample and judging whether a peptide in the subject sample is phosphorylated or not,
   wherein,
   the noble metal compound has substituents of following formula (I) on a side opposite to a side contacting the prism, and
   a subject sample is added to a side having the substituent groups (I) in the noble metal compound

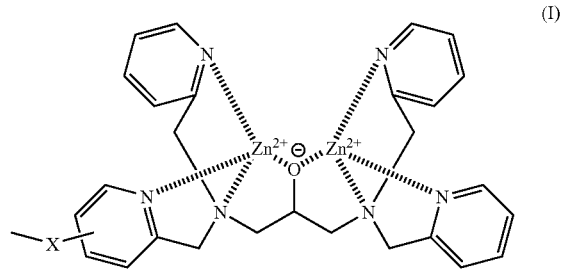

[wherein, X represents a linker group].

2. A method for measuring a surface plasmon resonance, comprising:
   adding a noble metal compound having substituents of formula (I) on a surface thereof to a subject sample, and using Raman spectroscopy,

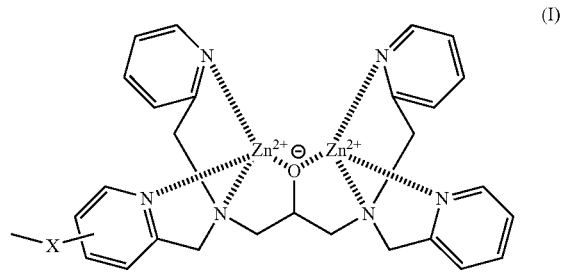

[wherein, X represents a linker group]
   for detecting a phosphorylated peptide in a subject sample and judging whether a peptide in the subject sample is phosphorylated or not.

* * * * *